United States Patent
Delisle

(10) Patent No.: US 7,264,585 B2
(45) Date of Patent: Sep. 4, 2007

(54) APPARATUS FOR TREATING BODY AILMENTS

(76) Inventor: Clarence A. Delisle, 1157 Villairo Avenue, Windsor, Ontario (CA) N8S 2K1

( * ) Notice: Subject to any disclaimer, the term of this patent is extended or adjusted under 35 U.S.C. 154(b) by 590 days.

(21) Appl. No.: 10/398,079

(22) PCT Filed: Sep. 28, 2001

(86) PCT No.: PCT/IB01/02335

§ 371 (c)(1),
(2), (4) Date: Mar. 28, 2003

(87) PCT Pub. No.: WO02/26322

PCT Pub. Date: Apr. 4, 2002

(65) Prior Publication Data

US 2005/0101827 A1  May 12, 2005

Related U.S. Application Data

(60) Provisional application No. 60/236,340, filed on Sep. 29, 2000.

(51) Int. Cl.
*A61N 1/00* (2006.01)

(52) U.S. Cl. .................................................... 600/14
(58) Field of Classification Search .............. 600/9–15; 128/897, 898
See application file for complete search history.

(56) References Cited

U.S. PATENT DOCUMENTS

| | | | | |
|---|---|---|---|---|
| 96,044 A | * | 10/1869 | Smith | 600/13 |
| 1,535,618 A | * | 4/1925 | Mayer | 335/293 |
| 1,922,696 A | * | 8/1933 | Hardage | 200/431 |
| 5,131,904 A | * | 7/1992 | Markoll | 600/14 |
| 5,669,868 A | * | 9/1997 | Markoll | 600/14 |

* cited by examiner

*Primary Examiner*—Samuel Gilbert
(74) *Attorney, Agent, or Firm*—Reising, Ethington, Barnes, Kisselle, P.C.

(57) ABSTRACT

An apparatus and a method for treating ailments of the human body by electromagnetic waves arm described. The body part to be treated is located inside an induction coil and the coil is energized from a storage battery through the special switching device. The switching device comprises a pair of metal rods one of which is hand-held by the operator and intermittently contacted with the other to apply successive pulses of current to the coil. The current pulses have a substantially rectangular waveform with a trailing edge produced by an arc discharge current when the switch is opened.

20 Claims, 1 Drawing Sheet

APPARATUS FOR TREATING BODY AILMENTS

This application is based on Provisional Application Ser. No. 60/236,340, filed Sep. 29, 2000.

FIELD OF THE INVENTION

This invention relates to method and apparatus for treating ailments of the human body; more particularly, it relates to an improved method and apparatus for using an electromagnetic field as a therapeutic agent for healing of pain relief of certain ailments such as arthritis.

BACKGROUND OF THE INVENTION

Therapeutic apparatus and methods using a magnetic field for treating various diseases including arthritis are already known in the prior art.

There are numerous teachings in the prior art for the application of a magnetic field to living tissue for healing and/or relief of pain. For example, U.S. Pat. No. 3,658,051, granted Apr. 25, 1972, discloses a process and apparatus for the treatment of human tissue where a body part to be treated is placed between the poles of an electromagnet. A pulsed magnetic field is applied to the body part which is induced in the electromagnet by an intermittent direct current. As further examples, U.S. Pat. No. 4,177,796, granted Dec. 11, 1979, U.S. Pat. No. 4,758,429, granted Jul. 19, 1988, and U.S. Pat. No. 5,314,400, granted May 24, 1994, disclose devices and methods for treating human joints, tissue, and various areas of the body using the application of a magnetic field.

Various processes and devices are known in the prior art for use in treating ailments and diseases in humans and in animals which utilize the magnetic field that may be induced by currents flowing through solenoids or coils. For example, the group of related patents comprises U.S. Pat. Nos. 5,131,904, granted Jul. 21, 1992, U.S. Pat. No. 5,453,073, granted Sep. 26, 1995, and U.S. Pat. No. 5,842,966, granted Dec. 1, 1998, disclose a process for the treatment of arthritis through the application of an electromagnetic field to a body part, where the device consists of a circular tube containing a coil, and where the coil segments are separated by air gaps. A pulsed DC voltage is applied to the coil which generates an electromagnetic field.

As a further example, U.S. Pat. No. 4,757,804, granted Jul. 19, 1988, discloses a method and apparatus for treating human tissue through the application of a pulsed magnetic field, where a flexible belt capable of carrying a pulsed electrical signal encircles the body part to be treated. The belt has a plurality of parallel conductors extending along its length to form at least one continuous coil.

A general object of this invention is to provide an improved method and apparatus for treatment of disease and pain in bodies of humans and animals by means of inducing electromagnetic fields of unique characteristics in the affected areas of the body. A further object is to overcome certain disadvantages of the prior art.

SUMMARY OF THE INVENTION

In accordance with this invention, a method and apparatus is provided for treating ailments of the human body or the body of other living creatures by applying an electromagnetic field to selected parts of the body. Further, in accordance with the invention, the body is treated by applying a sequence of electromagnetic pulses to the selected part of the body, each of said electromagnetic field pulses having substantially rectangular shape with a leading edge starting at zero value and increasing to a maximum value, said leading edge being followed by a substantially constant value which is followed by a trailing edge comprising a complex waveform which starts at said substantially constant value and decreases to zero, said complex waveform containing a spectrum of frequency components corresponding to current fluctuations substantially similar to those of an arc discharge.

Further, in accordance with this invention, apparatus is provided for applying an electromagnetic field to a body part and comprises, an induction coil for inducing an electromagnetic field in said body part, a voltage source, a switch having a closed and an open state, said induction coil and said voltage source being coupled together in a series circuit through said switch when said switch is in said closed state whereby current flows through said coil, said current being of sufficient magnitude that an arc discharge is generated in the atmosphere when the state of said switch is changed from said closed state to said open state, whereby an electromagnetic field pulse is produced in said coil when said switch is actuated from said open state to said closed state and back to said open state, said electromagnetic field pulse including a portion with a complex waveform including multiple frequency components having the same frequency components as said current pulse.

The inventor has discovered that therapeutic effects can be produced in the human body by subjecting a selected part of the body to electromagnetic waves which are generated in a particular manner. In particular, such electromagnetic waves can be generated by an electric current in an induction coil, said current consisting of pulses each having a substantially rectangular wave form of which the trailing edge is generated by an arc discharge current. The discovery was made by the inventor in the course of his efforts in trying to, relieve pain in his own arthritic ankle. In this effort, he tried applying static magnetic fields of various strengths without success. In order to subject his ankle to a magnetic field with a strength which he could control, he wound an induction coil around his ankle with the intention of producing a strong static magnetic field. For this purpose, he applied a voltage to the coil from an ordinary car battery through a conventional electric switch. This experiment failed because the switch contacts burned due to excessive current. The inventor replaced the conventional switch with a pair of rod-like conductors which were hand-held and manually actuated. When the rod-like switch contactors were engaged, a very large current was conducted through the induction coil and when the contactors were separated an arc discharge was generated between the contactors until the energy of the magnetic field of the coil was dissipated. The inventor found, by continued treatment of his ankle with this apparatus, that it provided a very significant beneficial effect on his arthritic ankle. Since that discovery the inventor has used the apparatus and method on a large number of persons seeking pain relief and hopefully cure of various ailments, especially arthritis. The inventor cannot explain why the method and apparatus of his invention has therapeutic value. However, it is his belief that this particular method and apparatus for generating the electromagnetic pulses produces at least some frequency components which interact with the human body in such manner as to provide healing and pain relief.

A complete understanding of this invention may be obtained from the description that follows taken with the accompanying drawings.

BEST MODE FOR CARRYING OUT THE INVENTION

Figure 1:
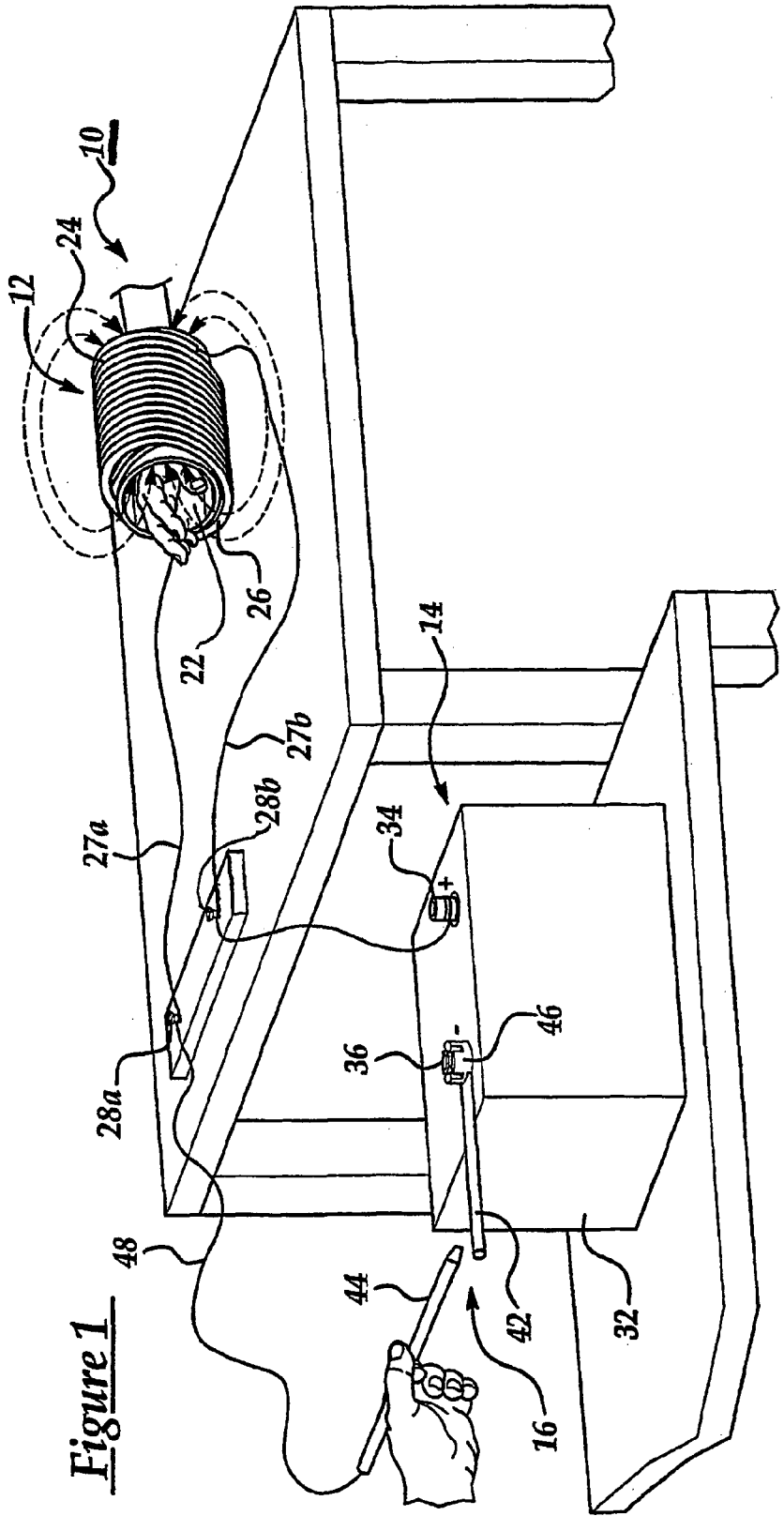
FIG. 1 depicts an electromagnetic wave treatment apparatus in accordance with the invention.

Referring now to the drawings, an illustrative embodiment of the apparatus and method of this invention will be described with reference to treatment of arthritis. It will be appreciated, as the description proceeds, that the invention is useful in many other applications and may be realized in a wide variety of embodiments.

As shown in FIG. 1, a magnetic treatment apparatus 10 comprises, in general, an induction coil 12 adapted to generate an electromagnetic field for application to a selected part of a person's body. The induction coil 22 is energized by a DC power source 14 through a switching device 16 in a series circuit arrangement.

The induction coil 12 comprises a coil-form 22 which supports a coil winding 24. The coil-form 22 is hollow and is constructed of insulating, non-magnetic material such as cardboard or plastic which is sufficiently rigid to support the coil winding 24 and to sustain its configuration. The hollow coil-form defines a space having a cross-sectional shape which is adapted to receive the selected part of the body which is to be treated such as the wrist, ankle, lower torso, etc. The coil winding 24 is wound with a single strand of magnet wire 26 which terminates in first and second wire ends 27a and 27b. The winding has multiple adjacent turns forming a helix extending axially of the coil-form with a plurality of layers as required to provide the desired number of turns. A terminal block adjacent the coil-form 22 includes a pair of binding posts 28a and 28b for facilitating connection of the coil winding to the power source 14 through the switching device 16. For this purpose, the wire end 27a is connected to the binding post 28a and the wire end 27b is connected to the binding post 28b.

The DC power source 14 in the illustrative embodiment suitably comprises a battery 32 having a positive terminal 34 and a negative terminal 36. The battery 14 is suitably a conventional 12 volt lead acid storage battery of the type currently used on automobiles for supplying current to the starter motor and other accessories; however, as discussed below, other types of power supplies may be used.

The switching device 16 comprises a fixed striking contactor 42 and a manually movable striking contactor 44. The fixed contactor 42 is a steel rod electrically connected to the negative terminal 36 of the battery 32 by a suitable battery clamp 46. The movable striking contactor 44 is also a steel rod which is electrically connected with one end of a flexible insulated copper wire 48. The other end of the wire 48 is connected with the binding post 28a of the coil winding 24. The movable striking contactor 44 is adapted to be handheld by the operator of the treatment apparatus for intermittent striking against the fixed striking contactor 42. The switching device 16 may also take the form of a conventional single pole, double throw switch as will be described below.

The method of this invention will now be described with reference to the treatment apparatus of FIG. 1. In preparation for treatment, the portion of the person's body to be treated, such as the hand, is inserted into the hollow space of the induction coil 12. In this location the hand is subjected to the maximum field of the induction coil. The treatment comprises the application of a sequence of electromagnetic field pulses over a period of time. Each electromagnetic pulse is generated under control of the person operating the treatment apparatus. Each pulse is produced by manual striking of the movable striking contactor 44 against the fixed contactor 42. The striking engagement of the contactors may be executed by the operator with variations of engagement force, duration and quickness of separation of the contactors. The pulse repetition rate may-also be varied by the operator such that the time between adjacent pulses may be substantially uniform or widely non-uniform. These variables in operation of the switching contactors enable the operator to exercise regulation of the strength of the electromagnetic field during a pulse, the duration of a pulse and the time between successive pulses in the pulse train generated during a treatment session. The operator may adjust one or more of the variables so as to subject the selected body part to more or less electromagnetic field strength in a time variable pattern in order to optimize the benefit of the treatment session. Also, the operator may need to exercise discretion in regard to possible overheating of the induction coil and the striking contactors by the current supplied to the coil. For example, applying large contact pressure to the contactors for an, extended time period may result in elevated temperatures which are uncomfortable to the person being treated or the operator. On the other hand, the current may be increased if desired by reducing the contact resistance of the contactors by wetting them with tap water or, in some cases, by removing metal oxides. Examples of electro-magnetic pulse patterns of treatment will be given below.

Figure 2:
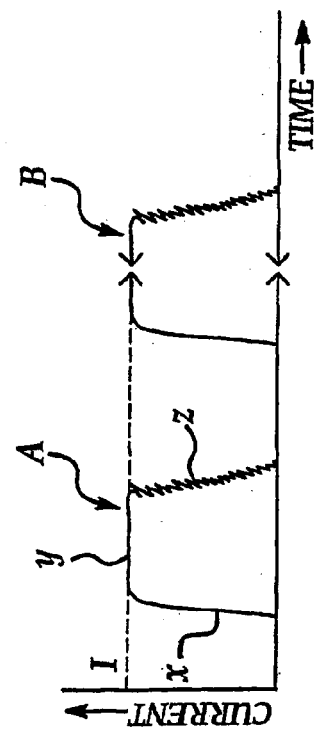
FIG. 2 shows a waveform diagram which represents the current in an induction coil which generates an electromagnetic wave in accordance with the invention.

The electromagnetic pulses produced by the treatment apparatus 10 of FIG. 1 are produced by current in the induction coil which varies as a function of time due to the operation of the switching device 16. The current waveform of each pulse can be characterized as a generally rectangular wave with a steep, approximately linear leading edge and a rapidly declining trailing edge which has a complex series of peaks and valleys generated during the separation of the contactors 42 and 44 of the switching device 16. FIG. 2 shows a representation of the waveforms A and B of two successive pulses which are produced by operation of the switching device 16. When the movable contactor 44 strikes the fixed contactor 42 the switching device 16 is in a closed state which initiates current through the contactors which rapidly increases in magnitude as represented by the leading edge x of the waveform A. The current waveform reaches a maximum value I and has a substantially flat top y and constant value until the movable contactor is separated from the fixed contactor which places the switching device in open state. Upon initial separation of the contactors the trailing edge z of the waveform commences and in a brief time interval, declines to zero. During the trailing edge, an arc discharge occurs in the air gap between the contactors due to the inductive impedance of the induction coil 12 which tends to maintain the current through the coil until the energy stored in the electromagnetic field of the coil has dissipated. The magnitude of the current I through the coil is sufficiently high so that the collapsing field of the coil generates a high voltage energy at a voltage spike as a back electromotive force high enough to ionize the air gap atmospheric gases which conduct the current until the energy in the field of the coil is dissipated. Thus, an arc discharge or plasma is generated in the atmospheric gases between the contactor while the magnitude of the current diminishes from the maximum value I to zero. This produces an arc discharge which is visible to the human eye in daylight. The current pulse B has the same waveform as pulse A except that it may be of longer or shorter duration as indicated by the arrow head interruption along the time axis of the waveform of pulse B.

The current pulses, as represented by pulses A and B, through the induction coil 12 generate electromagnetic field pulses corresponding to the current fluctuations. The electromagnetic field produced by each pulse has its greatest magnetic field strength concentrated in the interior space of the coil-form while a weaker magnetic field is produced in the space surrounding the outside of the coil-form. The leading edge x of the current pulse produces an electromagnetic field which includes a wide spectrum of electromagnetic wave frequency components. During the interval of the flat top y of the waveform, the current may be substantially constant or may undergo relatively small variations due to changing contact resistance between the contactors (arising, for example, from relative movement of the contactors). Consequently, during the flat top y portion of the waveform the electromagnetic field is predominately a static magnetic field to the extent that the current flow remains constant. During the interval of the trailing edge z, a complex current waveform is generated which is initiated by the high energy voltage spike as discussed above. This complex current waveform produces a corresponding complex electromagnetic waveform. At the termination of the trailing edge of the waveform, the coil returns to a quiescent state.

The generation of the electromagnetic field by the treatment apparatus 10 will now be discussed more specifically. An important parameter in the design of the induction coil 12 in conjunction with the selected power source 14 is the ampere turns AT to be used for generating the electromagnetic field of the coil. The value of AT is the product of the number of turns in the coil and the number of amperes delivered to the coil by the power source. The magnetic flux density B, in Teslas (T) generated at a point, including the center of the coil or solenoid, is given by B=kNI, where k is a parameter that depends upon the geometry, N is the number of turns in the coil, and I is current through the coil, in amperes. This relationship is valid for DC as well as for time dependent currents up to frequencies that involve magnetic resonance of molecules. The magnetic field strength H, which produces magnetic flux in a material, is created when current passes through a coil. It is related to the magnetic flux density in a material by B=μ·H, where μ (mu) is the permeability, a parameter that defines the effect of H inside the material. In ferrous materials, such as carbon steel, the permeability can be 1000 or more. The permeability in air, or in the human body is 1, depending on the choice of units. Thus, a given electromagnetic field strength can be produced by a coil with a small number of turns and a large current or a coil with a large number of turns and a small current. In the electric circuit of FIG. 1, a 12 volt battery is described as the power source. In the electric circuit of FIG. 1, the current through the coil 12 is determined largely by the voltage supplied by the power source 14 and the circuit resistance. The electrical resistance of the circuit is due to the resistance of the wire 26 and the contact resistance of contactors 42 and 44 with metal oxide accumulation on the surfaces. The resistance of the wire is a linear function of the wire cross-sectional area which may be expressed in a wire gage number.

The treatment apparatus 10 may be adapted to different therapeutic applications by interchangeable induction coils 12 and power supplies 10. For example, a set of storage batteries 14 having different voltage and current ratings may be selectively substituted for the battery 14 as described above. Similarly, a set of induction coils 12 of different size and shape and having a different wire size and number of windings may be substituted for the induction coil 12. The following table lists a set of six different induction coils of different physical size and having coil windings of different number of turns. This table also shows the part of the body for which it is applicable.

| COIL NO. | LENGTH | DIA-METER | WIRE GAGE | WIRE LENGTH | USE |
|---|---|---|---|---|---|
| 1 | 8" | 3" | 10 | 35' | small hands and elbows |
| 2 | 8" | 4" | 10 | 45' | large hands and elbows |
| 3 | 8" | 6" | 10 | 60' | shoulders and knees |
| 4 | 8" | 10" | 10 | 60' | shoulders and knees |
| 5 | 8" | 42" | 10 | 80' | shoulders |
|  | 8" | 60" | 10 | 100' | hips |

Induction coil #1 in the above table produces an electromagnetic field strength having a maximum value at the center of the coil of about 700 oersteds when the coil is energized by 12 volts across its terminals. Induction coil #6 in the above table produces a field strength having a maximum value at the inside periphery of the coil winding of about 2000 oersteds when the coil is energized with 12 volts across its terminals.

As described above, the striking contactors 42 and 44 are actuated manually to provide a switching of the treatment apparatus between on and off conditions. For turning the circuit on, the contactors are put in contact with each other and for turning the circuit off they are separated from each other. The contactors are switched on and off intermittently to generate current pulses. The sequential intermittent switching may be executed randomly in respect to on and off time intervals at the discretion of the operator. Also, the duration of the on time and the off time may be executed in accordance with a predetermined pattern. One preferred pattern for the treatment of arthritis, for example, comprises a sequence as follows: on-time one second duration followed by successive on-times of about one-tenth second spaced by time intervals of about one-tenth second. This pattern can be accomplished by a rubbing action of the movable contactor against the fixed contactor to produce the initial long pulse followed by a tapping action of the movable contactor against the fixed contactor in a continuous motion to produce about fifteen short interval pulses. Then this pattern is repeated for about three minutes with about fifteen seconds between patterns. This set of patterns may then be repeated several times in the discretion of the operator.

The inventor has treated seventy different persons with the treatment apparatus and method of this invention. Some of these people were treated for complaints of arthritis, multiple sclerosis carpal tunnel, rotor cuff, tennis elbow and cancer. The inventor believes the treatments have been effective to reduce pain, produce curative effects and provide an improved quality of life.

CONCLUSION

Although the description of this invention has been give with reference to particular embodiments, it is not to be construed in a limiting sense. Many variations and modifications of the invention will now occur to those skilled in the art.

What is claimed is:

1. A method of treating an ailment of the body of a living creature, comprising the steps of:
    selecting a part of the body related to the ailment;
    subjecting the body part to a sequence of electromagnetic field pulses,
    each of said electromagnetic field pulses having substantially rectangular shape with a leading edge starting at zero value and increasing to a maximum value, said leading edge being followed by a substantially constant value which is followed by a trailing edge comprising a complex waveform which starts at said substantially constant value and decreases to zero, said complex waveform containing a spectrum of frequency components corresponding to current fluctuations substantially similar to those of an arc discharge.

2. The method as defined in claim 1 wherein said pulses have time duration in the range of about one millisecond to about one second.

3. The method as defined in claim 2 wherein the time interval between pulses is in the range of about one second to about ten seconds.

4. The method as defined in claim 1 wherein the electromagnetic pulses have a magnetic field strength in the range of about 500 to about 2000 oersteds.

5. Apparatus for applying an electro-magnetic field to a selected part of the body of a living creature, said apparatus comprising:
    an induction coil for inducing a magnetic field in said selected part, a voltage source, and a switch having a closed and an open state,
    said induction coil being formed from multiple adjacent turns of wire wherein each turn encircles a space having a cross-sectional shape adapted to receive the selected part of the body,
    said induction coil and said voltage source being coupled together in a series circuit through said switch when said switch is in said closed state whereby current flows through said coil, said current being of sufficient magnitude that an arc discharge is generated in the atmosphere when the state of said switch is changed from said closed state to said open state, whereby an electromagnetic field pulse is produced in said coil when said switch is actuated from said open state to said closed state and back to said open state, said electromagnetic field pulse including a portion with a complex waveform including multiple frequency components generated by said arc discharge.

6. The apparatus as defined in claim 5 wherein the switch comprises a pair of striking contactors, at least one of which is manually movable into and out of contact with the other striking contactor.

7. The apparatus as defined in claim 5 wherein the switch comprises a single pole switch.

8. Apparatus for applying an electro-magnetic field to a selected part of the body of a living creature, said apparatus comprising:
    an induction coil for inducing a magnetic field in said selected part, a voltage source, and a switch having a closed and an open state,
    said induction coil being formed from multiple adjacent turns of wire wherein each turn encircles a space having a cross-sectional shape adapted to receive the selected part of the body,
    said induction coil and said voltage source being coupled together in a series circuit through said switch when said switch is in said closed state whereby current flows through said coil, said current being provided as a series of pulses produced by moving the switch between the open and closed states, said current pulses having a trailing edge that includes a complex current waveform, whereby an electromagnetic field pulse is produced in said coil when said switch is actuated from said open state to said closed state and back to said open state, said electromagnetic field pulse including a portion with a complex waveform that corresponds to said complex current waveform.

9. The apparatus as defined in claim 8 wherein the switch comprises a pair of striking contactors, at least one of which is manually movable into and out of contact with the other striking contactor.

10. The apparatus as defined in claim 8 wherein the switch comprises a single pole switch.

11. Apparatus for applying a magnetic field to a selected part of the body of a living creature, said apparatus comprising:
    a hollow coil-form defining a space having a cross-sectional shape and adapted to receive said selected part of said body with said coil-form encircling said part,
    a coil-winding comprising an electrical conductor supported by said coil-form, said conductor terminating in first and second ends,
    a DC voltage source having first and second terminals,
    said first end of said wire being electrically coupled to said first terminal,
    a first striking contactor of conductive material conductively coupled with said second end of said wire, wherein said first striking contactor is a manually movable rod,
    a second striking contactor of conductive material conductively coupled with said second terminal,
    said first striking contactor being movable into contact with said second striking contactor for making a conductive contact therebetween and being movable out of contact with said second striking contactor for breaking said conductive contact therebetween,
    said voltage source supplying current flow through said contactors and said coil when said contactors make said conductive contact therebetween, said current flow being of sufficient magnitude that a plasma is generated that is visible to the human eye in daylight when said contactors are moved out of contact with each other, whereby a current pulse is produced in said coil by moving said contactors in and out of contact with each other, said current pulse producing an electromagnetic field pulse having a complex waveform including multiple frequency components having the same frequency components as said current pulse.

12. The apparatus as defined in claim 11 wherein said coil-winding comprises multiple adjacent turns of wire extending around said coil form and forming a helix that encircles said space.

13. The apparatus as defined in claim 11 wherein said conductor is a wire.

14. The apparatus as defined in claim 11 wherein said voltage source is a battery.

15. The apparatus as defined in claim 11 wherein the electromagnetic pulse has a magnetic field strength in the range of about 500 to about 2000 oersteds.

16. The apparatus as defined in claim 11 wherein said second contactor is fixed.

17. A method of treating an ailment of the body of a living creature, comprising the steps of:

selecting a part of the body related to the ailment;

subjecting the body part to a sequence of electromagnetic field pulses generated by current pulses having a trailing edge comprising a complex waveform which starts at an upper value and falls towards zero, the complex waveform having frequency components corresponding to current fluctuations substantially similar to those of an arc discharge.

18. The method set forth in claim 17, wherein said subjecting step further comprises generating the current pulses using a switching device.

19. The method set forth in claim 18, wherein the switching device comprises a pair of striking contactors.

20. The method set forth in claim 18, wherein the switching device comprises a switch.

* * * * *